United States Patent
Adamson et al.

(10) Patent No.: US 10,760,076 B2
(45) Date of Patent: Sep. 1, 2020

(54) USE OF SINGLE-STRANDED ANTISENSE OLIGONUCLEOTIDE IN PREVENTION OR TREATMENT OF GENETIC DISEASES INVOLVING A TRINUCLEOTIDE REPEAT EXPANSION

(71) Applicant: ProQR Therapeutics II B.V., Leiden (NL)

(72) Inventors: Peter Adamson, Leiden (NL); Janne Juha Turunen, Leiden (NL); Gerardus Johannes Platenburg, Leiden (NL)

(73) Assignee: ProQR Therapeutics II B.V., Leiden (NL)

( * ) Notice: Subject to any disclaimer, the term of this patent is extended or adjusted under 35 U.S.C. 154(b) by 152 days.

(21) Appl. No.: 15/765,864

(22) PCT Filed: Oct. 5, 2016

(86) PCT No.: PCT/EP2016/073817
§ 371 (c)(1),
(2) Date: Apr. 4, 2018

(87) PCT Pub. No.: WO2017/060317
PCT Pub. Date: Apr. 13, 2017

(65) Prior Publication Data
US 2018/0282724 A1    Oct. 4, 2018

(30) Foreign Application Priority Data

Oct. 5, 2015 (GB) .................................. 1517565.6
Mar. 11, 2016 (GB) .................................. 1604253.3

(51) Int. Cl.
| | | |
|---|---|---|
| C12N 15/113 | (2010.01) | |
| A61P 27/02 | (2006.01) | |
| A61K 9/00 | (2006.01) | |
| A61K 31/7105 | (2006.01) | |

(52) U.S. Cl.
CPC .......... *C12N 15/113* (2013.01); *A61K 9/0019* (2013.01); *A61K 9/0048* (2013.01); *A61K 31/7105* (2013.01); *A61P 27/02* (2018.01); *C12N 2310/11* (2013.01); *C12N 2310/315* (2013.01); *C12N 2310/321* (2013.01); *C12N 2320/32* (2013.01)

(58) Field of Classification Search
CPC .......... C12N 2310/11; C12N 2310/315; C12N 2310/321; C12N 2310/3521; A61K 9/0048; A61P 27/00
USPC .................. 435/6.1, 91.1, 455, 458; 514/44; 536/23.1, 24.5
See application file for complete search history.

(56) References Cited

U.S. PATENT DOCUMENTS

2013/0317088 A1*  11/2013  Cheng .................. A61K 31/713
514/44 A

FOREIGN PATENT DOCUMENTS

| EP | 2049664 B1 | 9/2011 | |
|---|---|---|---|
| EP | 2425814 B1 | 6/2013 | |
| WO | WO-2008018795 A1 * | 2/2008 | ........... C12N 15/113 |
| WO | WO-2009099326 A1 | 8/2009 | |
| WO | WO-2011113889 A1 | 9/2011 | |
| WO | WO-2013101711 A1 | 7/2013 | |
| WO | WO-2014/011053 A1 | 1/2014 | |
| WO | WO-2014062686 A1 | 4/2014 | |
| WO | WO 2014062691 | 4/2014 | |

OTHER PUBLICATIONS

Armakola et al. (2012) "Inhibition of RNA lariat debranching enzyme suppresses TDP-43 toxicity in ALS disease models," Nat. Genet., 44(12):1302-9.
Baratz et al. (2010) "E2-2 protein and Fuch's corneal dystrophy," N. Engl. J. Med., 363(11):1016-1024.
Batra et al. (2014) "Loss of MBNL1 leads to disruption of developmentally regulated alternative polyadenylation in RNA-mediated disease," Mol. Cell, 56(2):311-22.
Cleary and Ranum. (2014) "Repeat associated non-ATG (RAN) translation: new starts in microsatellite expansion disorders," Curr. Opin. Genet. Dev., 26:6-15.
Du et al. (2015) "RNA toxicity and missplicing in the common eye disease Fuch's endothelial corneal dystrophy," J. Biol. Chem., 290(10):5979-90.
Egholm et al. (1993). "PNA hybridizes to complementary oligonucleotides obeying the Watson-Crick hydrogen-bonding rules," Nature, 365(6446): 566-8.
Garcia et al. (2014) "Identification of genes in toxicity pathways of trinucleotide-repeat RNA in C. elegans," Nat. Struct. Mol. Biol., 21(8):712-20.
Gattey et al. (2014) "Fuchs endothelial corneal dystrophy in patients with myotonic dystrophy: a case series," Cornea, 33(1):96-98.
George et al. (2000) "Gene delivery to the corneal endothelium," Am. J. Respir. Crit. Care. Med., 162:S194-200.
Govindaraju et al. (2005) "Backbone-extended pyrrolidine peptide nucleic acids (bepPNA): design, synthesis and DNA/RNA binding studies," Chem. Commun. (Camb), (4):495-7.
International Search Report for PCT/EP2016/073817, dated Dec. 23, 2016 (5 pages).
Jahromi A et al. (2013) "Developing bivalent ligands to target CUG triplet repeats, the causative agent of Myotonic Dystrophy Type 1," J. Med. Chem., 56(23):9471-9481.
Kuot A et al. (2012) "Association of TCF4 and CLU polymorphisms with Fuchs' endothelial dystrophy and implication of CLU and TGFBI proteins in the disease process," Eur. J. Hum. Genet., 20(6):632-8.
Li et al. (2011) "Replication of TCF4 through association and linkage studies in late-onset Fuchs endothelial corneal dystrophy," PLoS One, 6(4):e18044.

(Continued)

*Primary Examiner* — Jane J Zara
(74) *Attorney, Agent, or Firm* — Fish & Richardson P.C.

(57) ABSTRACT

The invention relates to antisense oligonucleotides (AONs) comprising repetitive trinucleotide units for use in the treatment or prevention of genetic eye diseases, preferably eye dystrophy disorders caused by RNA toxicity such as Fuch's Endothelial Corneal Dystrophy (FECD). The oligonucleotides of the present invention are used to target trinucleotide repeat (TNR) sequence expansions present in intron sequences, to prevent the disease-related sequestration of cellular proteins that interact with such TNR expansions.

6 Claims, 6 Drawing Sheets
Specification includes a Sequence Listing.

(56) References Cited

OTHER PUBLICATIONS

Li-Pook-Than and Bonen. (2006) "Multiple physical forms of excised group II intron RNAs in wheat mitochondria," Nucleic Acids Res., 34(9):2782-90.

Mankodi et al. (2003) "Ribonuclear inclusions in skeletal muscle in myotonic dystrophy types 1 and 2," Ann. Neurol., 54(6):760-8.

Mootha et al. (2014) "Association and familial segregation of CTG18.1 trinucleotide expansion of TCF4 gene in Fuchs' endothelial corneal dystrophy," Invest. Ophtalmol. Vis. Sci., 55(1):33-42.

Mootha et al. (2015) "TCF4 triplet repeat expansion and nuclear RNA foci in Fuchs endothelial corneal dystrophy," Invest. Ophthalmol. Vis. Sci., 56(3):2003-11.

Morita et al. (2001) "2'-O,4'-C-Ethylene-bridged nucleic acids (ENA) with nuclease resistance and high affinity for RNA," Nucleic Acids Res. Suppl., (1):241-242.

Mulders et al. (2009) "Triplet-repeat oligonucleotide-mediated reversal of RNA toxicity in myotonic dystrophy," Proc. Natl. Acad. Sci., 106(33):13915-20.

Nakano et al. (2008) "Connexin43 knockdown accelerates wound healing but inhibits mesenchymal transition after corneal endothelial injury in vivo," Invest. Ophthalmol. Vis. Sci., 49(1):93-104.

Nanda et al. (2014) "Genetic association of TCF4 intronic polymorphisms, CTG18.1 and rs17089887, with Fuchs' endothelial corneal dystrophy in an Indian population," Invest. Ophthalmol. Vis. Sci., 55(11):7674-80.

Nielsen et al. (1991) "Sequence-selective recognition of DNA by strand displacement with a thymine-substituted polyamide," Science, 254(5037):1497-1500.

Peh et al. (2013) "Optimization of human corneal endothelial cell culture: density dependency of successful cultures in vitro," BMC Res. Notes, 6:176.

Peh et al. (2015) "The effects of Rho-associated kinase inhibitor Y-27632 on primary human corneal endothelial cells propagated using a dual media approach," Sci. Rep., 5:9167.

Pettersson et al. (2015) "Molecular mechanisms in DM1—a focus on foci," Nucleic Acids Res., 43(4):2433-41.

Savkur et al. (2001) "Aberrant regulation of insulin receptor alternative splicing is associated with insulin resistance in myotonic dystrophy," Nat. Genet., 29(1):40-7.

Sepp et al. (2012) "Pitt-Hopkins syndrome-associated mutations in TCF4 lead to variable impairment of the transcription factor function ranging from hypomorphic to dominant-negative effects," Hum. Mol. Genet., 21(13):2873-88.

Stamler et al. (2013) "Confirmation of the association between the TCF4 risk allele and Fuchs endothelial corneal dystrophy in patients from the Midwestern United States," Ophthalmic Genet., 34(1-2):32-4.

Sundin et al. (2006) "A common locus for late onset Fuchs corneal dystrophy maps to 18q21.2-q21.32," Invest. Ophthalmol. Vis. Sci., 47(9):3919-3926.

Suzuki et al. (2006). "Characterization of RNase R-digested cellular RNA source that consists of lariat and circular RNAs from pre-mRNA splicing," Nucleic Acids Res., 34(8):e63.

Thalamuthu et al. (2011) "Association of TCF4 gene polymorphisms with Fuchs' corneal dystrophy in the Chinese," Invest. Ophthalmol. Vis. Sci., 52(8):5573-8.

Wheeler et al. (2007) "Correction of CIC-1 splicing eliminates chloride channelopathy and myotonia in mouse models of myotonic dystrophy," J. Clin. Invest., 117(12):3952-7.

Wieben et al. (2012) "A common trinucleotide repeat expansion within the transcription 4 (TCF4, E2-2) gene predicts Fuchs corneal dystrophy," PLoS One, 7(11):e49083.

Wieben et al. (2014) "Comprehensive assessment of genetic variants within TCF4 in Fuchs' endothelial corneal dystrophy," Invest. Ophtalmol. Vis. Sci., 55(9):6101-6107.

Winchester et al. (1999) "Characterization of the expression of DMPK and SIX5 in the human eye and implications of pathogenesis in myotonic dystrophy," Hum. Mol. Genet., 8(3):481-492.

Written Opinion for PCT/EP2016/073817, dated Dec. 23, 2016 (6 pages).

Xing et al. (2014) "Transethnic replication of association of CTG18.1 repeat expansion of TCF4 gene with Fuchs' corneal dystrophy in Chinese implies common causal variant," Invest. Ophthalmol. Vis. Sci., 55(11):7073-8.

Vasanth, et al., "Expansion of CTG18.1 trinucleotide repeat in TCF4 is a potent driver of Fuchs' Corneal Dystrophy," Investigative Opthalmology & Visual Science, 2015, 56(8):4531-4536.

* cited by examiner

Fig. 2

GAGCTGAGTGATTTACTGGATTTCAGTGCGGTAAGAAAGAACGGTGGAAACTAACAACAGCT
GTGAAAAAAACAAAACAAAAACCCAAACACTTCAGCTAGAAACCAGTAGGAATCTAAAGGAC
AGTAATAATTTTAATTGGCTGAATCCTTGGTAAATATGAAGGTCTTTTTGACAAGTTTTTA
ACTATAATTTTGTGGTGTGATGGAAGATTCAGGCTTTTTTTTTTTTGAGTTTTATTACTG
GCCTTCAATTCCCTACCCACTGATTACCCCAAATAATGGAATCTCACCCCAGTGGAAAGCAA
AAATAGACACCCCTAAAACTAAACCACCCCTAAAACTTGGCCATGTCTGAACACTGAGACTA
CTAATACTTTGCACACTACTCTTCGTTTTATTTATTGTTTTTGGAAATGGAAAATAGAAAAT
AGGAGACCCAGTTGTCTCTTTAAAGTTTTAAGCTAATGATGCTTTGGATTGGTAGGACCTGT
TCCTTACATCTTACCTCCTAGTTACATCTTTTCCTAGGATTCTTAAAACTAGTATGGATATG
CTGAGCATACATTCTTTAGAACCTTTTGGACTGTTTTGGTAAATTTCGTAGTCGTAGGATCA
GCACAAAGCGGAACTTGACACACTTGTGGAGTTTTACGGCTGTACTTGGTCCTTCTCCATCC
CTTTGCTTCCTTTTCCTAAACCAAGTCCCAGACATGTCAGGAGAATGAATTCATTTTTAATG
CCAGATGAGTTTGGTGTAAGATGCATTTGTAAAGCAAAATAAAAAGAATCCACAAAACACAC
AAATAAAATCCAAACCGCCTTCCAAGTGGGGCTCTTTCATG**CTGCTGCTGCTGCTGCTG
CTGCTGCTGCTGCTGCTGCTGCTGCTGCTGCTGCTGCTGCTGCTGCTG**CTCCTCCTCCT
CCTCCTCCTTCTCCTCCTCCTCCTCCTCTTCTAGACCTTCTTTTGGAGAAATGGCTTTCGGA
AGTTTTGCCAGGAAACGTAGCCCTAGGCAGGCAGCTTTGCAGCCCCCTTTCTGCTTGTTGCA
CTTTCTCCATTCGTTCCTTTGCTTTTTGCAGGCTCTGACTCAGGGAAGGTGTGCATTATCCA
CTAGATACGTCGAAGAAGAGGGAAACCAATTAGGGTCGAAATAAATGCTGGAGAGAGAGGGA
GTGAAAGAGAGAGTGAGAGTGAGAGAGAGAGAGTCTTGCTTCAAATTGCTCTCCTGTTAG
AGACGAAATGAGAATTTAGTGCAGGTGGCACTTTTATTTTATTTGGGTTCACATATGACAG
GCAAATCCTATACGAGATGGAAATGGACATTGCCACGTTTATGGCCAAGGTTTTCAATATAA
AACAAAACAACTTTTTTCTTCTCCTTGGTGAAACTAGTGTTTTTCTAGAGAGGCTGCTGGCC
TCCAACCTGAATCTTGATAACATTATGGGGACTGTGTTTGTTCCAAATGTAGCAGTAGTACT
GCTTGGCCATCTAATGAACCTGAGGAAAAGAAAGAACAGAGTGATAATGGGGGCTGGGGTG
GGATCTGTAATGTTGTTTCTCTTTTAGTTTTAAGTTGGATGGTGATGTATTTACTAAATAA
ACCCTTAGCATAAACTCTAAGCTGTTTGGTAACAGTATGAAAGATCTTTGAGGAGCTCTGAA
GGCACAAGTGTCTTCTTTTCAACTGTAATATTTCTTTGTTTCTTTTAGATGTTTTCACCTCC
TGTGAGCAGTGGGAAA

Fig. 3

| | |
|---|---|
| mRNA: | 5'- CUGCUGCUGCUGCUGCUGCUG - 3' (SEQ ID NO:2) |
| AON: | 5'- CAGCAGCAGCAGCAGCAGCAG - 3' (SEQ ID NO:3): 7 repeats |
| | 5'- CAGCAGCAGCAGCAGCAG - 3' (SEQ ID NO:4): 6 repeats |
| | 5'- CAGCAGCAGCAGCAG - 3' (SEQ ID NO:5): 5 repeats |
| | 5'- CAGCAGCAGCAG - 3' (SEQ ID NO:6): 4 repeats |
| | 5'- CAGCAGCAG - 3' (SEQ ID NO:101): 3 repeats |
| | 5'- AGCAGCAGCAGCAGCAGC - 3' (SEQ ID NO:7): 7 repeats |
| | 5'- AGCAGCAGCAGCAGC - 3' (SEQ ID NO:8): 6 repeats |
| | 5'- AGCAGCAGCAGC - 3' (SEQ ID NO:9): 5 repeats |
| | 5'- AGCAGCAGC - 3' (SEQ ID NO:10): 4 repeats |
| | 5'- AGCAGCAGC - 3' (SEQ ID NO:102): 3 repeats |
| | 5'- GCAGCAGCAGCAGCAGCAGCA - 3' (SEQ ID NO:11): 7 repeats |
| | 5'- GCAGCAGCAGCAGCAGCA - 3' (SEQ ID NO:12): 6 repeats |
| | 5'- GCAGCAGCAGCAGCA - 3' (SEQ ID NO:13): 5 repeats |
| | 5'- GCAGCAGCAGCA - 3' (SEQ ID NO:14): 4 repeats |
| | 5'- GCAGCAGCA - 3' (SEQ ID NO:103): 3 repeats |
| | 5'- CAICAICAICAICAICAICAI - 3' (SEQ ID NO:15): 7 repeats |
| sAON: | 5'- CUGCUGCUGCUGCUGCUGCUG - 3' (SEQ ID NO:16): 7 repeats |

Fig. 5
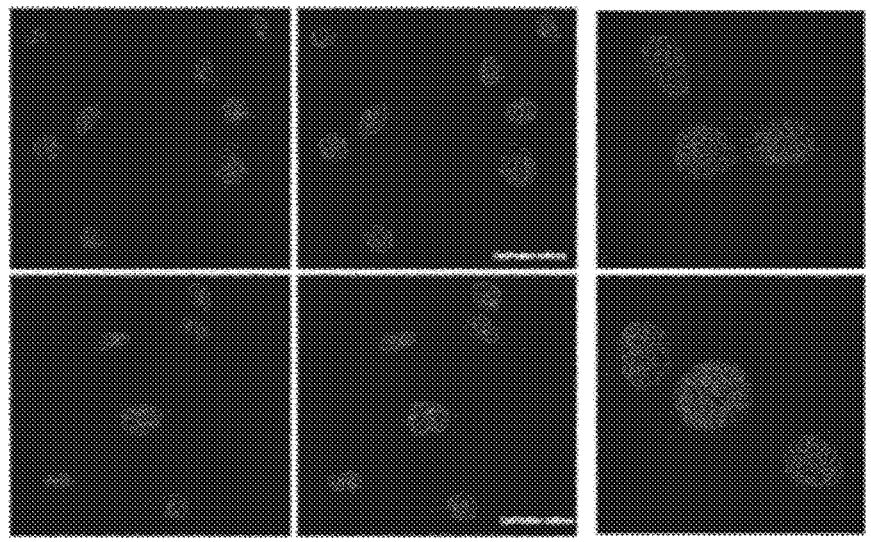
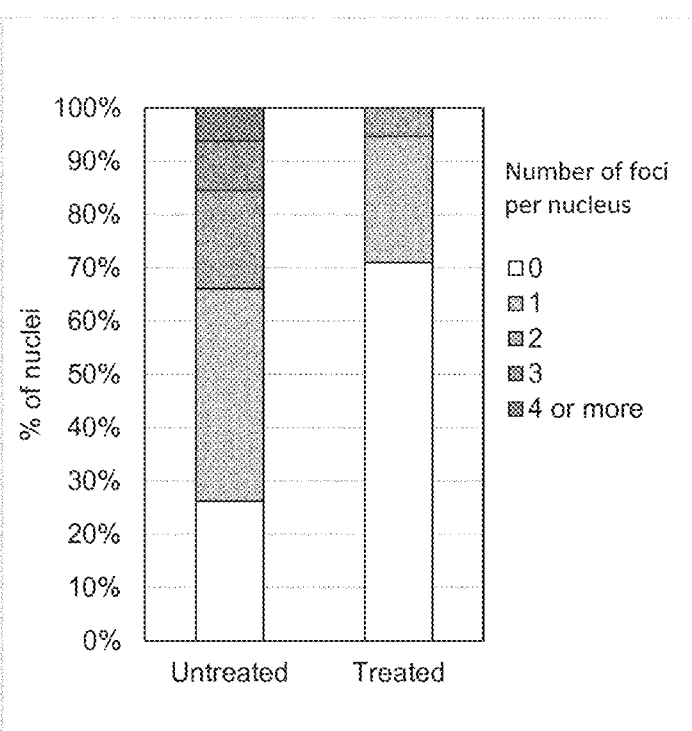

USE OF SINGLE-STRANDED ANTISENSE OLIGONUCLEOTIDE IN PREVENTION OR TREATMENT OF GENETIC DISEASES INVOLVING A TRINUCLEOTIDE REPEAT EXPANSION

RELATED APPLICATIONS

This application is a § 371 National Stage Application of PCT/EP2016/073817, filed Oct. 5, 2016, which claims priority to and the benefit of United Kingdom patent application No. 1517565.6, filed Oct. 5, 2015, and United Kingdom patent application No. 1604253.3, filed Mar. 11, 2016, the entire disclosures of each of which are incorporated herein by reference for all purposes.

FIELD OF THE INVENTION

The present invention relates to the field of medicine, in particular to the field of preventing and treating genetic disorders. More in particular, the present invention relates to the prevention and/or treatment of genetic diseases associated with trinucleotide repeat expansions, such as corneal endothelial disorders.

BACKGROUND OF THE INVENTION

The corneal endothelium is a non-regenerative cell monolayer on the internal surface of the cornea, separating the corneal stroma from the anterior chamber fluid (see FIG. 1). The corneal endothelium is responsible for maintenance of corneal clarity by a continual process that prevents excessive hydration of cornea from an influx of cations and water molecules into the collagenous corneal stroma, generally referred to as 'deturgescence'.

Fuchs Endothelial Corneal Dystrophy (FECD) is a common inherited, corneal endothelial degeneration disorder associated with the presence of corneal guttae, which are microscopic collagenous accumulations under the corneal endothelial layer. After the age of 40, up to 5% of US adults exhibit corneal guttae. The presence of guttae is indicative of FECD but generally represents mild disease that is completely asymptomatic. Advanced (severe) disease develops in a small proportion of patients with guttae. Advanced FECD is characterized by extensive guttae, endothelial cell loss, corneal edema, corneal clouding and consequential vision loss due to corneal edema and clouding. Corneal edema, clouding and subsequent vision loss are a direct consequence of endothelial cell degeneration and loss of deturgescence. Vision loss due to FECD is the most frequent indication requiring full thickness corneal transplantation (penetrating keratoplasty), accounting for greater than 14,000 procedures annually in the US alone. No other treatments are available for FECD. Although corneal transplantation is a largely successful treatment it has the disadvantage that it is invasive and associated with approximate 30% rejection rate, which is not dissimilar to other solid organ allografts. An alternative approach in which just the corneal endothelium is replaced (endokeratoplasty) can also be carried out, but only by very experienced surgeons. Both interventions suffer from lack of donor material, either transplantable corneal buttons or corneal derived endothelial cells derived from donor corneas. FECD is also a risk for other procedures such as cataract surgery and is contraindicated for refractive surgery such as Laser-Assisted in situ Keratomileusis (LAISK) as these techniques lead to additional corneal endothelial cell loss.

FECD segregates into early-onset FECD and age-related FECD, which may be different diseases since guttae are not typically present in early-onset FECD. Early-onset FECD is rare and has been linked to genes such as Col82A2, encoding the α2-subunit of collagen VIII, a component of the endothelial basement membrane. In age-related FECD certain rare autosomal dominant mutations have been found in different genes, such as KCNJ13 (a potassium channel), SLC4A11 (a sodium-borate co-transporter) and ZEB1 (the Zinc-finger E-box homeodomain protein 1). Importantly however, the genetic basis of the majority of autosomal dominant age-related FECD has been attributed to the Transcription factor-4 (TCF4) gene following a genome-wide association study (Baratz K H et al. E2-2 protein and Fuch's corneal dystrophy. *N Engl J Med* 2010 363:1016-1024). In these studies a Single-Nucleotide Polymorphism (SNP) was identified within an intron of the TCF4 gene: rs613872 on chromosome 18q21.2, which segregated specifically in age-related FECD patients. The increase in the risk of FECD development is calculated as a 30 fold increase in homozygous subjects and the rs613872 marker was able to discriminate between cases and controls with 76% accuracy. At least two regions of the TCF4 locus have been associated with development of FECD, following prior observations of FECD associating with a chromosomal region located at 18q21.2-18q21.32 (Sundin O H et al. A common locus for late onset Fuchs corneal dystrophy maps to 18q21.2-q21.32. *Invest Ophthalmol Vis Sci* 2006 47:3919-3926). Several other studies illustrated that the presence of a TCF4 trinucleotide repeat (TNR) was more predictive of FECD than the rs613872 marker (Wieben E D et al. A common trinucleotide repeat expansion within the transcription 4 (TCF4, E2-2) gene predicts Fuchs corneal dystrophy. *PLoS One* 2012 7:e49083; Wieben E D et al. Comprehensive assessment of genetic variants within TCF4 in Fuchs' endothelial corneal dystrophy. *Invest Ophthalmol Vis Sci* 2014 55:6101-6107; Mootha V V et al. Association and familial segregation of CTG18.1 trinucleotide expansion of TCF4 gene in Fuchs' endothelial corneal dystrophy. *Invest Ophthalmol Vis Sci* 2014 55:32-42; Stamler J F et al. Confirmation of the association between the TCF4 risk allele and Fuchs endothelial corneal dystrophy in patients from the Midwestern United States. *Ophthalmic Genet.* 2013 34(1-2):32-4; Kuot A et al. Association of TCF4 and CLU polymorphisms with Fuchs' endothelial dystrophy and implication of CLU and TGFBI proteins in the disease process. *Eur J Hum Genet.* 2012 20(6):632-8; Thalamuthu A et al. Association of TCF4 gene polymorphisms with Fuchs' corneal dystrophy in the Chinese. *Invest Ophthalmol Vis Sci.* 2011 52(8):5573-8; Xing C et al. Transethnic replication of association of CTG18.1 repeat expansion of TCF4 gene with Fuchs' corneal dystrophy in Chinese implies common causal variant. *Invest Ophthalmol Vis Sci.* 2014 55(11):7073-8; Nanda G G et al. Genetic association of TCF4 intronic polymorphisms, CTG18.1 and rs17089887, with Fuchs' endothelial corneal dystrophy in an Indian population. *Invest Ophthalmol Vis Sci.* 2014 55(11):7674-80).

Unstable repeats are found in a variety of gene regions, such as in the coding region of the gene causing Huntington's disease (HD), whereby the phenotype of the disease is brought about by alteration of protein function and/or protein folding. Unstable repeat units are also found in non-coding regions, such as in the 3'-UTR of the DMPK gene causing Myotonic Dystrophy type 1 (DM1), in the 5'-UTR in the FMR1 gene causing Fragile X syndrome, and in intron sequences such as in the first intron of the ZNF9 gene causing Myotonic Dystrophy type 2 (DM2). DM1 is the most common muscular dystrophy in adults and is an inherited, progressive, degenerative, multi-systemic disorder of predominantly skeletal muscle, heart and brain. DM1 is caused by expansion of an unstable trinucleotide (CTG)n repeat (as noted above, in the 3'-UTR of the DMPK gene). DM2 is caused by a tetranucleotide (or quatronucleotide) (CCTG)n repeat (a quatronucleotide repeat hereinafter being referred to as "QNR") expansion (as noted above, in intron 1 of the ZNF9 gene). Instability of TNRs is also found to be the predominant cause of several other disorders, such as X-linked Spinal and Bulbar Muscular Atrophy (SBMA), several spinocerebellar ataxias (SCA gene family), C90RF72-associated Amyotrophic Lateral Sclerosis, Frontotemporal Dementia (C90RF72 ALS/FTD), and FECD.

Excessive TNR expansions may lead to a phenomenon referred to as 'RNA toxicity', which is the predominant cause of the diseases mentioned above. What happens is that these repetitive elements are transcribed into toxic 'gain-of-function' RNAs, which manifest as dominant-negative pharmacology, in which a single disease allele may already cause the disease despite the presence of a normal allele. In the case of DM1, RNA toxicity becomes manifest at the level of mRNA processing when splice regulators, such as the MuscleBlind-Like 1 (MBNL1) protein and CUG-triplet repeat binding protein 1 (CUGBP1) are sequestered from their normal cellular function: the proteins bind to the excess TNRs. Such protein-RNA complexes can be visualized in DM1 cells as nuclear RNA foci (Mankodi et al. Ribonuclear inclusions in skeletal muscle in myotonic dystrophy types 1 and 2. *Ann Neurol* 2003 54(6):760-8). MBNL1 is a splicing regulator but also binds 3'-UTRs, which therefore also leads to mis-regulation of alternative polyadenylation in DM1 (Batra et al. Loss of MBNL1 leads to disruption of developmentally regulated alternative polyadenylation in RNA-mediated disease. *Mol Cell* 2014 56(2):311-22). Recent reports suggest that repeat RNAs may be translated into toxic protein species (Cleary and Ranum. Repeat associated non-ATG (RAN) translation: new starts in microsatellite expansion disorders. *Curr Opin Genet Dev* 2014 26:6-15).

FECD was observed to be associated with a (CTG)n TNR expansion in an intron region of the TCF4 gene that is different from the intron in which the rs613872 marker is located (Mootha et al. 2014; Wieben et al. 2012). It was shown that 79% of FECD patients (noted in leukocyte DNA) had 50 or more repeats (150 nucleotides), whereas 95% of case controls had repeat lengths of less than 40, which shows that a repeat length of 50 or more is highly predictive of FECD, whereas fewer repeats, between 40 and 50, also contribute to appearance of the disease. It is generally accepted in the field that the appearance of a TNR expansion at a size equal or greater than 40 repeats in the TCF4 gene is predictive of disease and indicative of a potential RNA toxicity mechanism leading to FECD (Du et al. RNA toxicity and missplicing in the common eye disease Fuch's endothelial corneal dystrophy. *J Biol Chem* 2015 290(10): 5979-90). RNA foci were identified in fibroblasts from FECD patients that were both homozygous and heterozygous for TNR expansions in the TCF4 gene. No RNA foci were found in fibroblasts from unaffected individuals. Unaffected individuals generally appear to carry wild type TCF4 genes with around 20 TNRs. Heterozygote FECD patients (with fibroblasts wherein RNA foci were detected) carried one normal length allele (20 TNRs) and one allele with an expansion of NM TNRs. In homozygote FECD patients both alleles contained ≥40 TNRs. Consequently fewer than 40 repeats in the TCF4 expanded TNR regions can be considered a non-disease causing genotype. RNA foci were also identified in the corneal endothelium of FECD patient samples, while none were found in unaffected individuals. The presence of such RNA foci appeared associated with a change in the RNA splicing patterns for a number of other genes (Du et al. 2015). These splicing pattern changes are consistent with similar changes noted in DM1 (Wheeler et al. Correction of ClC-1 splicing eliminates chloride channelopathy and myotonia in mouse models of myotonic dystrophy. *J Clin Invest* 2007 117(12):3952-7; Savkur R S et al. Aberrant regulation of insulin receptor alternative splicing is associated with insulin resistance in myotonic dystrophy. *Nat Genet* 2001 29(1):40-7; Li Y J et al. Replication of TCF4 through association and linkage studies in late-onset Fuchs endothelial corneal dystrophy. *PLoS One.* 2011 6:e18044). The general conclusion is that the majority of FECD cases is caused by RNA toxicity in the corneal endothelial cells due to the presence of TNR expansions in intronic RNA derived from the TCF4 gene. RNA toxicity was found in patients that were either heterozygous or homozygous for the extended repeat, and is likely the result of sequestration of proteins that interact with the RNA harboring the TNR expansions. Such proteins—through this sequestration—can no longer perform their normal function in the cells.

Despite the good results that can be achieved with full corneal transplantation or transplantation of the endothelial layer to treat FECD, it is clear that such procedures still encounter great disadvantages, which have been outlined above. Hence, there remains an unmet medical need to treat patients suffering from, or that are at risk of developing FECD, preferably by means that are a proper alternative for transplantation.

SUMMARY OF THE INVENTION

The present invention relates to an antisense oligonucleotide (AON) for use in the prevention and/or treatment of a genetic disease, preferably in a human subject suffering from said genetic disease, or at risk of suffering from said genetic disease, wherein said oligonucleotide is at least partially complementary to a target RNA molecule, and wherein said oligonucleotide is capable of binding a trinucleotide repeat (TNR) expansion present in an intron sequence within said target RNA molecule. Said genetic disease is preferably caused by RNA toxicity, wherein the RNA transcribed from the intron sequence and which comprises the TNR expansion sequesters cellular proteins such that those can no longer perform their normal function within the cell. A preferred genetic disease that is treated and/or prevented by using the AONs of the present invention is an eye dystrophy in humans, more preferably a disease referred to as Fuchs Endothelial Corneal Dystrophy (FECD) that is caused by a TNR expansion in the TCF4 gene. In a preferred aspect, said TNR expansion comprises the sequence 5'-(CUG)n-3', wherein n is an integer of 40 or greater, preferably 50 or greater. In yet another preferred embodiment, the AON for use according to the invention comprises the sequence 5'-(CAG)m-3', wherein m is an integer ranging from 2 to 66, preferably wherein m is an integer of 2, 4, 5, 6, 7, 8, 9, 10, 11, 12, 13, 14, 15, 16 or 17. The present invention also relates to the AONs as defined herein, and to pharmaceutical compositions comprising any one of the AONs as disclosed herein.

In another embodiment, the present invention relates to a method of treating or preventing FECD in a human subject, said method comprising administering an oligonucleotide according to the invention, or a composition according to the invention, to the corneal stroma of said human subject by intrastromal injection, or to the anterior chamber fluid of said human subject by intracameral injection, or to the posterior chamber of said human subject by intravitreal injection.

BRIEF DESCRIPTION OF THE DRAWINGS

FIG. 2 provides the human TCF4 intron 3 sequence (SEQ ID NO:1) of a healthy individual with 24 CTG repeats (bold). Flanking exon sequences are underlined.

FIG. 3 shows examples of antisense oligonucleotide sequences (AONs) and part of their complement in intron 3 of the human TCF4 gene. SEQ ID NO:2 represent (part of) the 5'-(CUG)n-3' repeat as it is found in the mRNA of intron 3 of the human TCF4 gene, in this case the CUG repeat is represented by a multifold of 7. SEQ ID NO:3-15 represent AONs according to the present invention. SEQ ID NO:101, 102 and 103 (so named because the sequence listing does not represent oligonucleotides shorter than 10 nucleotides and these 3 AONs are 9 nucleotides in length) also represent AONs according to the present invention. SEQ ID NO:16 represents a control oligonucleotide, which represents the sense strand comprising the CUG repeat, similar to SEQ ID NO:2.

FIG. 5 shows the effect of therapeutic oligonucleotide (CAG)7 (upper three panels) in reducing RNA foci (pink spots) in human corneal endothelial cells derived from an FECD patient with a heterozygous expansion of greater than 40 CUG repeats in the TCF4 gene. Controls are shown in the lower three panels with foci still clearly visible. Therapeutic oligonucleotide was used at a concentration of 200 nM and transfected with Dharmafect. RNA foci were identified using fluorescence in situ-hybridisation (FISH) using a Cy3-labelled (CAG)7 oligonucleotide probe. The number of RNA foci in the nuclei of cell examined was determined by automated image analysis and displayed as a histogram (bottom of figure). As can be observed from both the micrographs and the histogram the therapeutic oligonucleotide (CAG)7 was effective in reducing the number of RNA foci compared to transfection of a control (irrelevant) oligonucleotide.

DETAILED DESCRIPTION OF THE INVENTION

Figure 1:
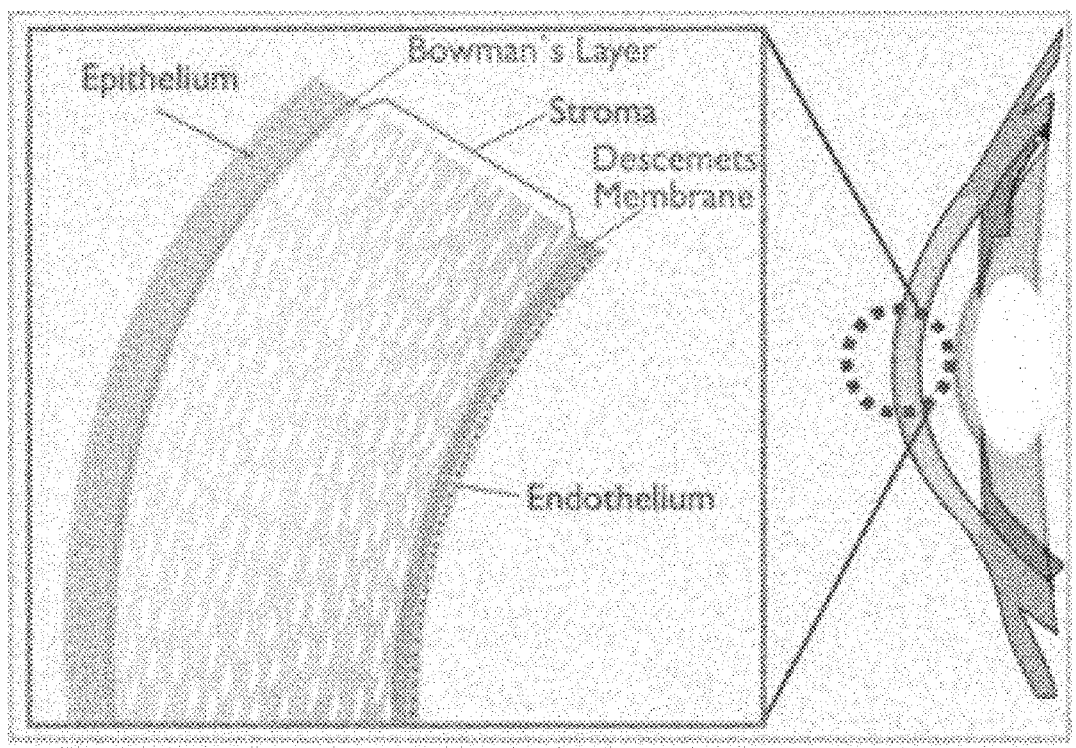
FIG. 1 is a schematic representation of the frontal part of the eye, showing (enlarged on the left) from left to right: the corneal epithelium layer on the outside of the eye, the Bowman's layer between the epithelium and the stroma, the corneal stroma, the Descemet's Membrane, the corneal endothelial layer and the anterior chamber fluid.

The present invention relates to methods and molecules that can be used in the prevention or treatment of genetic diseases, preferably diseases caused by RNA toxicity, more preferably diseases of the eye that are the result of RNA toxicity. More in particular, the present invention relates to antisense oligonucleotides (AONs) for use in treating diseases associated with the sequestration of proteins involved in splicing regulation, such as MBNL1, in particular through binding of such proteins to excessive TNR expansions present in an intron of a precursor mRNA. A preferred disease that is treated with the AONs of the present invention is Fuchs Endothelial Corneal Dystrophy (FECD), which is associated with the occurrence of excessive TNR expansions in intron 3 of the TCF4 transcript, causing excessive binding of the splice regulating protein MBNL1 to such excessive TNR expansions. In other words, and in a preferred aspect, the present invention relates to AONs for use in the prevention or treatment of FECD, by administering AONs that bind to the excessive TNR expansion in the transcripts of the TCF4 gene, thereby preventing the unwanted binding of proteins to the excessive TNR expansion. A hallmark of MBNL1 binding to excessive TNR expansions is the formation of so-called RNA foci in the nucleus of diseased cells of a patient. Hence, the AONs of the present invention are used to treat or prevent genetic (eye) diseases such as FECD, by removal or preventing the formation of RNA foci, particularly in corneal endothelial cells.

FIG. 2 shows the sequence of intron 3 (5' to 3' of the coding strand) of the human TCF4 gene of a healthy individual, plus a stretch of exon sequences at the 5' and 3' ends. As outlined above, the presence of CTG repeat expansions in intron 3 of the TCF4 gene associated with FECD development is well known in the art. WO2011/101711 discloses a method for detecting (in human samples) these CTG-repeat expansions using oligonucleotide primers and PCR amplification. The oligonucleotides and methods disclosed in WO2011/101711 are used to diagnose patients with FECD or at risk of developing FECD, and to determine whether an individual should avoid undergoing corneal transplantation or laser correction. It is noted that WO2011/101711 does not disclose or suggest methods to prevent the development or alleviate the symptoms of FECD.

As outlined above, also DM1 is a disease resulting from RNA toxicity, and EP2049664B1 discloses methods for treating DM1 using AONs targeting TNR expansions in transcripts of the human DMPK gene. EP2049664B1 discloses AONs having the sequence 5'-(CAG)n-3' to treat a variety of human cis-element repeat instability associated disorders, such as HD, spinocerebellar ataxia, Haw River syndrome, X-linked spinal and bulbar muscular atrophy and dentatorubral pallidoluysian atrophy, DM1, spinocerebellar ataxia type 8, and Huntington's disease type 2. The TNR repeat expansions in DM1 are found in the 3'-UTR of the DMPK gene. Others describe the use of (CAG)7 AONs to target transcripts of exon 15 of the human DMPK gene correlated with DM1 (Mulders et al. 2009. *Triplet-repeat oligonucleotide-mediated reversal of RNA toxicity in myotonic dystrophy*. Proc Natl Acad Sci USA 106(33):13915-20). The authors assume that both the cytoplasmic pool of mRNA, as well as the nuclear pool of primary and mature expanded (CUG)n transcripts served as targets.

DM1 is an RNA-toxicity mediated disease and toxic DMPK pre-mRNAs contain expanded TNRs with the same repeating unit (CUG) as the TCF4 transcript in FECD patients. It may seem that MBNL1 is sequestered in DM1 patients in a similar fashion as in FECD patients. It is therefore attractive to assume that DM1 and FECD can be treated in the same way with the same AONs. However, it is important to note that there is a difference between the RNA toxicity process occurring in DM1 and FECD. In DM1, proteins are sequestered by binding to 3'-UTR RNA sequences, that are present not only in primary transcripts, but also in the mature RNA (when introns have already been spliced out), and may thus be located in either the nucleus or in the cytoplasm. In FECD on the contrary, the RNA toxicity is caused by sequestration of proteins binding to intronic RNA, either as part of primary pre-mRNA or, more likely as intronic RNA that has been spliced out of the mature mRNA, in both cases being retained in the nucleus. Hence, the cellular compartments where the oligonucleotides that act in the treatment of DM1 are different from where they act in the case of FECD. It is, therefore, not immediately self-evident that an AON approach would work in FECD in the same way as in DM1, as the AONs to be used to treat FECD, or any other intronic TNR expansion related disease for that matter, will have to function exclusively in a different compartment of the cell (i.e. in the nucleus), at a different stage of processing and transportation of the transcript. Besides, it is not self-evident whether or how efficiently the sequestrated proteins, such as MBNL1 will be released upon AON treatment. A salient difference in FECD compared to DM1 is that MBNL1 is assumed to bind to the spliced out, non-degraded intron lariats, which are processed with different kinetics than exon sequences, including exon sequences in RNA comprising 3'-UTRs and 5'-UTRs.

Interestingly, the inventors of the present invention came to realize that, if sequestration of MBNL1 or other factors common to these RNA foci are mechanistically involved in pathology of FECD, then DMPK containing TNR expansions should convey a similar risk of developing FECD if DMPK is found to be expressed in the corneal endothelium. Interestingly, DMPK is in fact expressed in the human eye (Winchester C L et al. Characterization of the expression of DMPK and SIX5 in the human eye and implications of pathogenesis in myotonic dystrophy. *Hum Mol Genet.* 1999 8:481-492) and FECD has been found in myotonic dystrophy patients: In a cohort of four DM patients each patient had bilateral FECD (Gattey D et al. Fuchs endothelial corneal dystrophy in patients with myotonic dystrophy: a case series. *Cornea* 2014 33:96-98). Also, it has been noted in post-mortem eyes from myotonic dystrophy patients that there is considerable loss of corneal endothelial cells which is a clinical hallmark of advanced FECD (Winchester et al. 1999). The inventors of the present invention also realized that DM1 patients who develop FECD can be treated for FECD using the AON approach disclosed herein. But, more importantly, the inventors of the present invention realized that, by targeting TCF4 transcripts with excessive TNR expansions in intron 3, as is the case in FECD patients, such patients can effectively be treated for FECD.

As mentioned above, DM2 is also a disease that is a result of an NR expansions (a QNR) in intron sequences. DM2 patients harbor QNR expansions in an intron of the ZNF9 gene. However, it appears that the RNA toxicity observed is different between DM2 and FECD. In DM2 there appears to be an accumulation of (unspliced) intronic RNA harboring the QNRs, which is caused by the fact that splicing of the ZNF9 RNA itself is blocked, which results in a reduction in the level of the transcript (and functional protein). In FECD there is no lack of functional TCF4 (see below).

The art does not teach the possibility to target (CUG) based TNR expansions residing in an intron, as is the case in the TCF4 transcript, and none of the discussed references disclose or suggest AONs for use in the prevention or therapy of corneal dystrophies, such as FECD. To elaborate further on this, the repeat expansions in DM1 cause formation of RNA foci that are predominantly nuclear, but can also be observed in the cytoplasm, depending on the genotype and cell type (Pettersson et al. Molecular mechanisms in DM1—a focus on foci. *Nucleic Acids Res* 2015 43(4):2433-41.). It has been found that after AON treatment, the repeat-containing DMPK RNA is quickly degraded (Mulders et al. 2009). The exact mechanism by which this happens is unknown, and likely depends, in part, on localization of the transcripts, which is affected both by the extent of RNA processing and transport that vary between cell types. Transcripts with un-spliced introns or incomplete polyadenylation are generally retained in the nucleus, and are eventually degraded by the nuclear exosome, hence detailing a fundamentally different mechanism of RNA degradation. Specifically, the CUG expansion in DM1 is known to result in RNA processing defects of the DMPK transcript, and such RNAs would thus likely be retained in the nucleus. However, involvement of the nonsense-mediated decay machinery, a cytoplasmic process, in degrading the repeat-containing RNA has also been shown in DM1, with the knockdown of a nonsense-mediated decay factor resulting in an increase also in the amount of nuclear DMPK foci (Garcia et al. Identification of genes in toxicity pathways of trinucleotide-repeat RNA in *C. elegans. Nat Struct Mol Biol* 2014 21(8):712-20). This indicates that a significant portion of the transcripts is processed efficiently, consistent with the observed location of DMPK mRNA in the cytoplasm in some cells. Thus, after being released from the nuclear foci, the DMPK transcripts are likely to be degraded by cytoplasmic as well as nuclear processes, although the relative extent of these processes remains unknown.

The situation regarding TCF4 expansions in FECD is different, as the foci have only been observed in the nucleus, likely because the repeats are located in an intron, which do not appear within mature transcripts that are exported to the cytoplasm. Hence, AONs targeting the TCF4 repeats exclusively act in the nucleus. Firstly, the localization, possibly within particular nuclear domains that are involved in the processing of introns (such as nuclear speckles), affects the delivery and activity of the AONs. Secondly, the position of the repeats itself (in an intron sequence) can affect the binding kinetics of MBNL1, which may be influenced by other proteins that also bind to the intron RNA. Both aspects, the nuclear localization and the fact that the TNRs are in an intron sequence, affect the ability of the AONs to act. One additional factor that should be taken into account is the stability of intron RNA sequences and the mechanisms by which such intron RNA is degraded after its release from the nuclear foci. RNA sequencing shows that RNA from the intron-containing repeats accumulates in FECD patient cells, while accumulation of RNA from other parts of the transcript is not observed (Du et. al. 2015). It furthermore appears that the expression levels of the TCF4 mRNA and protein are not significantly altered by the extended repeats, as haploinsufficency of TCF4 causes another, more severe disorder known as Pitt-Hopkins syndrome (Mootha et al. TCF4 triplet repeat expansion and nuclear RNA foci in Fuchs endothelial corneal dystrophy. *Invest Ophthalmol Vis Sci* 2015 56(3):2003-11; Sepp et al. Pitt-Hopkins syndrome-associated mutations in TCF4 lead to variable impairment of the transcription factor function ranging from hypomorphic to dominant-negative effects. *Hum Mol Genet* 2012 21(13): 2873-88.). This suggests that the observed nuclear foci are composed mainly of spliced-out intron RNA that sequesters the proteins such as MBNL1. During the splicing reaction, the intron's branch-point adenosine becomes linked to the nucleotide at the splicing donor site by an unconventional 2'-5' phosphodiester linkage, forming a branched lariat structure. These structures are relatively stable in the nucleus, and require additional steps for their degradation. In a normal situation, specific protein factors release the splicing factors that still remain bound to the lariats. Following this, a specific lariat debranching enzyme, DBR1, is recruited to the complex to open up the 2'-5' phosphodiester linkage. Following the debranching, the released linear intronic RNAs are degraded by the nuclear exosome and/or the exonuclease XRN1. It is hypothesized by the inventors of the present invention that complexation of TCF4 RNA with MBNL1 (and possibly other repeat-binding proteins) in the nuclear foci prevents one or several of the steps required for lariat debranching and degradation. Thus, in contrast to the situation with DMPK, the release of the repeat-containing TCF4 RNA and the associated proteins from the nuclear foci during the treatment of FECD have different kinetics. The same is true of the subsequent degradation of the RNA itself, and the RNA may require additional processing and optimization to be effectively cleared.

To the inventors' knowledge, this is the first time that it is disclosed that a disease associated with an excessive intronic TNR expansion can be treated using AONs that are complementary to the TNR, effectively binding such TNR expansion causing the release of splice regulating proteins, such as MBNL1, in the nucleus of the cells of a diseased patient, thereby removing the RNA toxicity. This is particularly useful to treat FECD, where the excessive TNR expansion resides in intron 3 of the TCF4 gene, especially now that it has been convincingly shown by the present inventors, that AONs can effectively be delivered to and taken up by the corneal endothelial cell layer. However, using reduction or disappearance of nuclear foci in the nucleus of a diseased cell as a marker of effectiveness, it is anticipated by the inventors of the present invention that treatment of other toxic gain of function RNAs involving intronic TNR expansions, may be treated using AONs targeting the same.

The present invention relates to an antisense oligonucleotide (AON), preferably a single strand AON, a composition comprising such AON, and to a pharmaceutical composition comprising such AON and a pharmaceutically acceptable excipient or carrier. The present invention also relates to a use of such AON or composition for in vivo or in vitro treatment or prevention of a disease that is caused by RNA toxicity, comprising administration of such AON or composition to a subject, preferably a human subject. The invention also relates to a method of treating and/or preventing a disease caused by RNA toxicity, preferably an eye dystrophy, more preferably FECD, comprising administration of such AON or composition to a subject, preferably a human subject.

It is preferred that an AON of the invention comprises one or more residues that are modified to increase nuclease resistance, and/or to increase the affinity of the AON for the target sequence. Therefore, in a preferred embodiment, the AON sequence comprises at least one nucleotide analogue or equivalent, wherein a nucleotide analogue or equivalent is defined as a residue having a modified base, and/or a modified backbone, and/or a non-natural internucleoside linkage, or a combination of these modifications. In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells.

According to one embodiment of the invention the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages. In accordance with this embodiment, a preferred nucleotide analogue or equivalent comprises a Peptide Nucleic Acid (PNA), having a modified polyamide backbone (Nielsen et al. 1991 *Science* 254:1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar 2005 *Chem Commun* 495-497). Since the backbone of a PNA molecule contains no charged phosphate groups, PNA-RNA hybrids are usually more stable than RNA-RNA or RNA-DNA hybrids, respectively (Egholm et al. 1993 *Nature* 365:566-568).

According to another embodiment of the invention, the backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or di-substituted at the 2', 3' and/or 5' position such as a —OH; —F; substituted or unsubstituted, linear or branched lower (C1-C10) alkyl, alkenyl, alkynyl, alkanyl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; -dimethylaminooxyethoxy; and -dimethylaminoethoxyethoxy. The sugar moiety can be a furanose or derivative thereof, or a deoxyfuranose or derivative thereof, preferably ribose or derivative thereof, or deoxyribose or derivative thereof. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-0,4'-C-ethylene-bridged nucleic acid (Morita et al. 2001 *Nucleic Acid Res* Supplement No. 1: 241-242). These substitutions render the nucleotide analogue or equivalent RNase H and nuclease resistant and increase the affinity for the target RNA.

It is understood by a skilled person that it is not necessary for all internucleosidic linkages in an antisense oligonucleotide to be modified. For example, some internucleosidic linkages may be unmodified, whereas other internucleosidic linkages are modified. AONs comprising a backbone consisting of one form of (modified) internucleosidic linkages, multiple forms of (modified) internucleosidic linkages, uniformly or non-uniformly distributed along the length of the AON are all encompassed by the present invention. In addition, any modality of backbone modification (uniform, non-uniform, mono-form or pluriform and all permutations thereof) may be combined with any form or of sugar or nucleoside modifications or analogues mentioned below. An especially preferred backbone for the AONs according to the invention is a uniform (all) phosphorothioate (PS) backbone.

In another embodiment, a nucleotide analogue or equivalent of the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an antisense oligonucleotide to be modified uniformly. In addition, more than one of the aforementioned analogues or equivalents may be incorporated in a single antisense oligonucleotide or even at a single position within an antisense oligonucleotide. In certain embodiments, an antisense oligonucleotide of the invention has at least two different types of analogues or equivalents.

According to another embodiment AONs according to the invention comprise a 2'-O (preferably lower) alkyl phosphorothioate antisense oligonucleotide, such as 2'-O-methyl modified ribose (RNA), 2'-O-methoxyethyl modified ribose, 2'-O-ethyl modified ribose, 2'-O-propyl modified ribose, and/or substituted derivatives of these modifications such as halogenated derivatives. An effective and especially preferred AON format according to the present invention comprises 2'-O-methyl modified ribose moieties with a phosphorothioate backbone, preferably wherein substantially all ribose moieties are 2'-O-methyl and substantially all internucleosidic linkages are phosphorothioate linkages.

An oligonucleotide according to the present invention contains a sequence complementary to (part of) the TNR expansion found in intronic sequences, and comprises a multitude of a sequence that is complementary to the triplet sequence in the expansion. Although a TNR may be referred to as a repeating sequence of CUG triplets (from 5' to 3'), the nature of DNA (and corresponding RNA) makes that such can also be written as UGC repeats or as GCU repeats, depending on what is considered to be the first nucleotide of the triplet. This means that the antisense oligonucleotides according to the invention may either start with any of the nucleotides that is complementary to one of the nucleotides in the triplet: CAG, GCA, or AGC (from 5' to 3'). Examples of antisense oligonucleotides that can be used according to the teaching of the present invention are provided in FIG. 3, indicating that any of the three nucleotides of the complementary sequence may be the first nucleotide. Targeting 5'-(CUG)n-3' TNRs in introns preferably takes place by using AONs with complementary sequences formed through canonical Watson-Crick base-pairs: 5'-(CAG)m-3', or through wobble base-pairs, such as 5'-(CAI)m-3', 5'-(CGG)m-3', 5'-(CGI)m-3', 5'-(CIG)m-3', 5'-(CII)m-3', 5'-(UAG)m-3', 5'-(UAI)m-3', 5'-(UGG)m-3', 5'-(UGI)m-3', 5'-(UIG)m-3' and 5'-(UII)m-3'. When the second nucleotide shifts one position towards the 5' end and becomes the first nucleotide of the repeat, the following repeated sequences are then contemplated: 5'-(AGC)m-3', 5'-(AIC)m-3', 5'-(GGC)m-3', 5'-(GIC)m-3', 5'-(IGC)m-3', 5'-(IIC)m-3', 5'-(AGU)m-3', 5'-(AIU)m-3', 5'-(GGU)m-3', 5'-(GIU)m-3', 5'-(IGU)m-3' and 5'-(IIU)m-3', When the third nucleotide takes the place of the first nucleotide then the following repeated sequences are contemplated: 5'-(GCA)m-3', 5'-(ICA)m-3', 5'-(GCG)m-3', 5'-(ICG)m-3', 5'-(GCI)m-3', 5'-(ICI)m-3', 5'-(GUA)m-3', 5'-(IUA)m-3', 5'-(GUG)m-3', 5'-(IUG)m-3', 5'-(GUI)m-3' and 5'-(IUI)m-3'. Clearly, in a CUG sequence that is repeated 40 or more times, one can also recognize UGC repeats and GCU repeats.

The current invention makes use of a molecule preferably an antisense oligonucleotide (AON), that is capable of binding a trinucleotide repeat (TNR) expansion that comprises the sequence 5'-(CUG)n-3', wherein n is long enough to cause RNA toxicity in a cell in which such TNR expansions are transcribed. The TCF4 gene is such a gene that, when comprising 40 or more of the TNRs, causes FECD by sequestration of normal cellular proteins to the TNR expansions in the cells of the corneal endothelium. However, the invention relates to the molecules, such as AONs for use in any disorder that is caused by the occurrence of TNR expansions in intronic sequences. The art does not teach how to treat or prevent genetic disorders in which RNA toxicity is brought about by TNR expansions in introns, especially not those that are caused by CUG TNR expansions. The nucleic acid molecules of the present invention consist of sequences that are complementary to the TNR.

Although the invention is exemplified using 'naked' or 'gymnotic' AONs as molecules that are capable of binding to a TNR expansion, persons having ordinary skill in the art will recognize that other molecules that are capable of binding to nucleic acid sequences, more in particular TNRs, yet more particularly 5'-(CUG)n-3' expansions are encompassed by the invention. Examples of such molecules are proteins, such as Zinc-Finger proteins, antibodies or antibody fragments, aptamers, bivalent ligands (Haghighat Jahromi A et al. Developing bivalent ligands to target CUG triplet repeats, the causative agent of Myotonic Dystrophy Type 1. *J Med Chem* 2013. 56:9471-9481) and the like. Also encompassed by the present inventors are AONs expressed from a vector, such as a DNA vector or a viral vector (e.g. adenoviral, AAV, or lentiviral vector) coding for a nucleic acid molecule that comprises or consists of an AON according to the invention.

The invention thus provides molecules for use in a method for the prevention and/or treatment of an unstable cis-element DNA repeat associated genetic disorder, preferably an eye dystrophy, more preferably FECD. The invention relates to a method comprising the step of providing nucleic acid molecules that are complementary to and/or capable of hybridizing to TNRs, preferably in intron regions. It is not essential that the RNA with which the nucleic acid molecules of the invention hybridize are degraded, as long as the proteins the sequestration of which is associated with the diseased state, are no longer, or at least to a relatively lower level, sequestered upon administration of the molecules according to the invention. This can be assessed by looking at the RNA foci inside the nucleus of the cell. In one aspect, the present invention discloses and teaches the use of an AON consisting of a sequence that is complementary only to a repetitive sequence in a human gene transcript for the manufacture of a medicament for the diagnosis, treatment or prevention of a cis-element repeat instability associated genetic disorder in mammalian subjects, preferably humans. In a preferred embodiment, the cis-element repeat instability associated genetic disorder is the result of RNA toxicity that is caused by RNA transcripts that contain TNRs in one or more intron sequences. In most preferred embodiment, said disease is FECD.

The oligonucleotides of the present invention are preferably single stranded, chemically modified and synthetically produced. Alternatively, they may be expressed inside a target cell, such as a corneal endothelial cell, from a nucleic acid sequence, such as delivered by a viral (e.g. lentiviral, AAV, or adenoviral) or non-viral vector. An AON according to the invention may be from 8 to 200 nucleotides in length, preferably between 10 and 100, more preferably between 12 and 50. The AONs according to the invention may comprise between 2 and 66 repetitive units consisting of 3 nucleotides, preferably 5, 6, 7, 8, 9, 10, 11, 12, 13, 14, 15, 16 or 17 of such repetitive units. A TNR comprises at least two repetitive units of identical repeating units of three nucleotides (=trinucleotide), which means that when a trinucleotide is repeated 3 times, the length of the TNR is at least 9 nucleotides and that when a trinucleotide is repeated 7 times, the length of the TNR is at least 21 nucleotides. The length of the TNR that causes disease is dependent of the disease, which, in the case of FECD is equal to or more than 40 repeats of the repeating unit, usually more than 45, even more usually more than 50, although this may differ from patient to patient. It should be clear that the AONs of the present invention are complementary to a number of repetitive units (a minimum of two) in the target RNA, but this does not mean the AONs have to consist of a multiple of 3 nucleotides. For example, the AON may comprise, in addition to a central portion that is complementary to two or more repeating units, 1 or 2 complementary nucleotides at one end (5' or 3') or both ends (5' and 3') of the AON. In other words, an AON of the invention may be entirely complementary to a sequence within a TNR expansion in a target RNA, while the complementary region of the AON does not consist of a multiple of 3. For example, an oligonucleotide of the present invention may be 9 nucleotides in length, yet comprise only 2 repetitive CAG units, see for instance SEQ ID NO:102 and SEQ ID NO:103, which indicates that the oligonucleotide of the present invention does not necessarily have to be a multifold of 3 nucleotides.

An important aspect of the present invention is the delivery of the AONs of the present invention to the corneal endothelium in the case of FECD. Therapeutic amounts of AONs can be dosed to the corneal stroma by intrastromal injection. Intrastromal injection is performed, for example, when administering an antibiotic to the cornea in the case of corneal keratitis. Alternatively, the therapeutic oligonucleotide can be dosed at the other side of the endothelial cell layer, into the aqueous humor by intra-cameral injection. As the anterior and posterior chamber of the eye are connected, the therapeutic oligonucleotide of the present invention can also be dosed in the posterior chamber of the eye by intravitreal injection. An illustration and example of this is provided in FIG. 4 in which an oligonucleotide coupled to a fluorescent dye (Cy5) is demonstrated to be specifically associated in with the corneal endothelial cell layer in a time-dependent manner after intravitreal injection. Association with the corneal endothelial layer appears maximal 48 h post injection. All routes of administration are acceptable, as long as they lead to uptake by the corneal endothelial cells. The ability of AONs to be taken-up by the corneal endothelium is nevertheless unexpected as many viral and non-viral vectors have been explored to deliver genes to the corneal endothelium but with limited success in vivo (George A J et al. *Am J Respir Crit Care Med.* 2000. 162:S194-200). Successful in vivo studies of endothelial gene delivery without using the injection procedure have not been reported in the literature. One successful approach utilizing injection into the anterior chamber has been demonstrated using connexin-43 anti-sense siRNA oligonucleotides injected into the anterior chamber (Nakano Y et al. Connexin43 knockdown accelerates wound healing but inhibits mesenchymal transition after corneal endothelial injury in vivo. *Invest Ophthalmol Vis Sci.* 2008. 49:93-104). However, since the function of the corneal endothelium is to maintain a leaky barrier to aid corneal stromal hydration, and this function is critically dependent on the presence of gap junctions, maintained in large part by connexin-43, it seems that this targeted knock-down contributes to the mechanism of oligonucleotide uptake into the corneal endothelium. Consequently, this is not to be regarded as a teaching that is generally applicable to other AONs. The efficacy of delivered therapeutic oligonucleotides will be dependent on the amount taken up into the cells from the corneal stroma, or the aqueous humour (even if first injected to the vitreous) and their ultimate delivery to the cell nucleus. Nuclear localization and efficiency of oligonucleotide uptake into cells is increased by the use of transfection reagents, or a so-called oligonucleotide delivery enhancing agent. In vivo transfection reagents are now available e.g. jetPEI (polyplus Transfection™) which is proposed to increase the uptake and nuclear localization of therapeutic oligonucleotides into corneal endothelium and represents an improvement over simply administering the therapeutic oligonucleotide as a "naked" molecule. Base pairing with the target RNA molecule occurs preferentially in the cell. For application in vivo, an oligonucleotide according to the invention may be packaged for delivery (administration) in a liposome, polysome, or nanoparticle or other suitable particle, such as a viral particle. Alternatively, or in combination with the delivery vehicles, the oligonucleotides might be complexed to polyethylene-imine (PEI) and/or polyethylene glycol (PEG). The person skilled in the art will comprehend that two or more oligonucleotides according to the present invention may be combined if applicable. The person skilled in the art will comprehend that when herein is referred to an oligonucleotide according to the invention, a composition or pharmaceutical composition according to the invention preferably can be interchangeably be used in the methods and uses according to the invention.

The present invention relates to a (single-stranded) AON for use in the prevention and/or treatment of a genetic disease, wherein said oligonucleotide is at least partially complementary to a target RNA molecule, and wherein said oligonucleotide is capable of binding a trinucleotide repeat (TNR) expansion present in an intron sequence within said target RNA molecule. In a preferred aspect, said TNR expansion comprises the sequence 5'-(CUG)n-3', wherein n is an integer of 40 or greater, more preferably wherein n is an integer of 50 or greater. In another preferred aspect, all nucleotides of the AON of the present invention are 2'-0 methyl phosphorothioate ribonucleotides.

In a particular preferred embodiment, an AON of the present invention comprises the sequence 5'-(CAG)m-3', 5'-(CAI)m-3', 5'-(CGG)m-3', 5'-(CGI)m-3', 5'-(CIG)m-3', 5'-(CII)m-3', 5'-(UAG)m-3', 5'-(UAI)m-3', 5'-(UGG)m-3', 5'-(UGI)m-3', 5'-(UIG)m-3', 5'-(UII)m-3', 5'-(AGC)m-3', 5'-(AIC)m-3', 5'-(GGC)m-3', 5'-(GIC)m-3', 5'-(IGC)m-3', 5'-(IIC)m-3', 5'-(AGU)m-3', 5'-(AIU)m-3', 5'-(GGU)m-3', 5'-(GIU)m-3', 5'-(IGU)m-3', 5'-(IIU)m-3', 5'-(GCA)m-3', 5'-(ICA)m-3', 5'-(GCG)m-3', 5'-(ICG)m-3', 5'-(GCI)m-3', 5'-(ICI)m-3', 5'-(GUA)m-3', 5'-(IUA)m-3', 5'-(GUG)m-3', 5'-(IUG)m-3', 5'-(GUI)m-3' or 5'-(IUI)m-3', wherein m is an integer ranging from 2 to 66, preferably wherein m is an integer of 2, 4, 5, 6, 7, 8, 9, 10, 11, 12, 13, 14, 15, 16 or 17. In another preferred aspect of the present invention the oligonucleotide of the invention has a length of 9 or more nucleotides.

The AONs of the present invention are preferably for use in the treatment and/or prevention of a genetic disease, wherein the TNR expansion causing the disease is present in a transcript of the TCF4 gene. One example of a disease caused by RNA toxicity due to TNR expansions in an intron sequence in the TCF4 gene is an eye dystrophy, preferably Fuchs Endothelial Corneal Dystrophy (FECD). Hence, in a preferred aspect, the AONs of the present invention are for use in the prevention and/or treatment of FECD. Preferably the AON for use according to the present invention is selected from the group consisting of the AONs with SEQ ID NO:3, 4, 5, 6, 7, 8, 9, 10, 11, 12, 13, 14, 15, 101, 102, and 103 (see FIG. 3). A preferred subject is a human subject. Although the AONs according to the present invention are for use in the treatment and/or prevention of the genetic disease(s) as defined herein, the invention also relates to the oligonucleotides itself that can be present in a pharmaceutical composition. The pharmaceutical composition according to the present invention preferably comprises an oligonucleotide as defined herein and a pharmaceutically acceptable excipient. Pharmaceutically acceptable excipients or carriers are well-known to the person skilled in the art. Since in a preferred aspect the AONs as described herein are delivered to tissues that may be difficult to penetrate by simple administration (such as the interior of an eye), the compositions of the present invention preferably comprise an oligonucleotide delivery enhancing agent. Although in certain aspects the AONs may be delivered directly or with the aid of a AON delivery enhancing agent, the AONs of the present invention may also be delivered by viral or non-viral gene delivery vehicles or gene therapy vectors such as outlined in detail in WO 2014/011053. Examples are adeno-associated virus (AAV) vectors, adenoviral vectors and lentiviral vectors. Non-viral gene delivery vehicles (or non-viral nucleic acid delivery vehicles) are for example liposomes, polysomes and nanoparticles.

In another embodiment, the present invention relates to a method of treating or preventing FECD in a human subject, said method comprising administering an oligonucleotide according to the invention, or a composition according to the invention, to the corneal stroma of said human subject by intrastromal injection, or to the anterior chamber fluid of said human subject by intracameral injection, or to the posterior chamber of said human subject by intravitreal injection.

In yet another embodiment, the invention relates to the use of an antisense oligonucleotide according to the invention for use in the preparation of a medicament for the treatment and/or prevention of a genetic disease, preferably a genetic disease caused by RNA toxicity, more preferably a genetic disease caused by RNA toxicity due to TNR expansions in intronic sequences, such as found in the human TCF4 gene, most preferably for the treatment and/or prevention of FECD in humans.

Non vectored AONs for uses as contemplated herein are typically to be used in dosages ranging from 0.0001 to 200 mg/kg, preferably from 0.001 to 100 mg/kg, more preferably from 0.01 to 50 mg/kg, depending on the disease, the target organ or tissue, and the route of administration.

For eye diseases, such as FECD a suitable dosage is upon intravitreal administration would be between 0.05 mg and 5 mg, preferably between 0.1 and 1 mg per eye, such as about per eye: 0.1, 0.2, 0.3, 0.4, 0.5, 0.6, 0.7, 0.8, 0.9 or 1.0 mg.

AONs according to the invention may be administered to a patient systemically, locally, topically, through administration that is orally, intraocularly, intrapulmonary, intranasally, intramuscularly, subcutaneously, intradermally, rectally, by swallowing, injecting, inhalation, infusion, spraying, in the form of (aqueous) solutions, suspensions, (oil-in-water) emulsions, ointments, lozenges, pills etcetera. A more preferred route of administration is through intracorneal injection of an aqueous solution or specially adapted formulation for intraocular administration. EP 2 425 814 discloses an oil in water emulsion especially adapted for intraocular (intravitreal) administration of peptide or nucleic acid drugs. This emulsion is less dense than the vitreous fluid, so that the emulsion floats on top of the vitreous, avoiding that the injected drug impairs vision.

Dosing may be daily, weekly, monthly, quarterly, once per year, depending on the route of administration and the need of the patient.

In a preferred embodiment, a viral vector, preferably an AAV vector as described earlier herein, as delivery vehicle for a molecule according to the invention, is administered in a dose ranging from $1 \times 10^9$-$1 \times 10^{17}$ virus particles per injection, more preferably from $1 \times 10^{10}$-$1 \times 10^{14}$, and most preferably $1 \times 10^{10}$-$1 \times 10^{12}$ virus particles per injection.

It will be clear to a person having ordinary skill in the art to which this invention pertains, that the details of treatment will need to be established in accordance with and depending on such factors as the sequence and chemistry of the oligonucleotide(s), the route of administration, the formulation, the dose, the dosing regimen, the format (vector or non-vectored AON), the age and weight of the patient, the stage of the disease and so forth, which may require further non-clinical and clinical investigation.

EXAMPLES

Example 1. Therapeutic Approach to Treating FECD Resulting from the Presence of TCF4 TNR Greater than 50 Repeats in Length By using anti-sense oligonucleotides (AONs) directed at the expanded CUG TNRs in TCF4, specific sequence binding is achieved, such that this results in reducing the ability of such sequences to sequester RNA processing factors such as MBNL1. The binding of the RNA may additionally result in its degradation due to release from nuclear foci and increased exposure to the lariat debranching enzyme and/or RNases, thus further reducing the cellular pool of repeat-containing RNA that can sequester RNA processing factors. In FECD, the sequestration of MBNL1 leads to toxic RNA foci and aberrant splicing patterns of other RNAs. Targeting 5'-(CUG)n-3' TNRs in TCF4 derived introns takes place by using AONs with complementary sequences formed either through canonical Watson-Crick base-pairs: 5'-(CAG)m-3', or through wobble base-pairs, such as 5'-(CAI)m-3', 5'-(CGG)m-3', 5'-(CGI)m-3', 5'-(CIG)m-3', 5'-(CII)m-3', 5'-(UAG)m-3', 5'-(UAI)m-3', 5'-(UGG)m-3', 5'-(UGI)m-3', 5'-(UIG)m-3' and 5'-(UII)m-3'. FIG. 3 provides examples of oligonucleotides which can be used to suppress the presence of TCF4 RNAs containing 50 or more CUG TNR sequences.

To screen for the therapeutic effect of the different AONs, they are transfected into patient-derived fibroblast or corneal cells, together with control (sense) AONs (bottom of FIG. 3). The disappearance of the nuclear RNA foci is verified by fluorescent in situ hybridization with a Cy3-labeled oligo, as well as by immunofluorescence with an anti-MBNL1 antibody.

Disappearance of the foci results from the reduced ability of the RNA to sequester MBNL1 and/or due to the reduced amount of RNA due to it becoming more accessible to RNA degrading enzymes, as observed for DMPK after AON treatment. It should be noted that the foci in FECD can be composed of either unspliced pre-mRNA, and/or spliced-out intronic lariats, or even partially degraded intronic RNA in which only the repeat sequences remain. This affects the stability and degradation kinetics of the RNA. To verify both the identity and stability of the repeat-containing RNA, northern blot analysis is carried out. In order to ascertain whether the observed bands are intron lariats, three separate approaches are used. Firstly, prior to AON treatment, the cells are depleted of the lariat debranching enzyme (DBR1) by RNAi, which results in stabilization of the lariats (Armakola et al. 2012. *Inhibition of RNA lariat debranching enzyme suppresses TDP-43 toxicity in ALS disease models.* Nat Genet 44(12):1302-9.). Secondly, after RNA isolation, RNA samples from AON or control-treated cells are subjected to RNAseR, which efficiently hydrolyzes linear RNA, but not the intron lariats (Suzuki et al. 2006. *Characterization of RNase R-digested cellular RNA source that consists of lariat and circular RNAs from pre-mRNA splicing.* Nucleic Acids Res 34(8):e63). Thirdly, in a complementary approach, the RNA samples are treated with RNaseH in the presence of DNA oligonucleotides complementary to specified positions within the TCF4 intron, such that hydrolysis by RNaseH results in cleavage of the unspliced intron into separate fragments, while the intron lariats are linearized (Li-Pook-Than and Bonen. 2006. *Multiple physical forms of excised group II intron RNAs in wheat mitochondria.* Nucleic Acids Res 34(9):2782-90).

RNA from AON treated cells and from control cells are analyzed for effects on RNA processing events known to be regulated by MBNL1. Initially, the effect of the AONs are verified by RT-PCR of selected transcripts whose splicing is known to be significantly affected by sequestration of MBNL1 into the nuclear foci in FECD (Du et al. 2015, supra). Following this, the restoration of splicing on transcriptome-wide level is analyzed by deep sequencing.

FISH and Immunofluorescence

For the detection of nuclear foci, FISH is performed essentially according to the protocol by Du et al. (2015): Fibroblasts and corneal tissue on coverslips are washed with PBS once and fixed in 4% paraformaldehyde in PBS for 30 min at RT. After fixation, cells are washed twice with PBS and stored in 70% ethanol at 4° C. Cells are rehydrated in 50% formamide and 2×SSC for 5 min at RT. The cells are then hybridized O/N at 37° C. in 100 µl of a mixture containing 10% dextran sulfate, 2 mM vanadyl-ribonucleoside complex, 0.2% BSA, 100 µg yeast tRNA, 2×SSC, 50% formamide, and 1.2 µg Cy3-(CAG)7 probe. After hybridization and washing, cells are stained with Hoechst 33342 (1:200 dilution) for 30 min at RT and mounted on the slide using ProLong Gold antifade reagent. The Cy3 signal is acquired at a magnification of 63 on a Zeiss LSM 710 laser scanning confocal microscope. After hybridization with the Cy3-(CAG)7 probe, the corneal endothelial layer is permeabilized with fresh PBS containing 0.5% Triton X-100 for 10 min. Corneal cells are then incubated with anti-MBNL1 antibody (1:100 in PBS; sc-47740, Santa Cruz Biotechnology) for 1 h at RT and with a secondary antibody conjugated with Alexa Fluor 488 (1:500 in PBS; A11001, Invitrogen) at RT for 30 min. Following incubation, corneal endothelial cells are washed with PBS, stained with Hoechst 33342, and mounted on a microscope slide as described above.

Northern Blots

Stability of TCF4 RNA variants from patient fibroblasts or corneal cells before and after AON treatment (and/or debranching enzyme DRB1 knockdown) is assayed by the Northern blot procedure used by Mulders et al (2009, supra). Total RNA from is electrophoresed in a 1.2% agarose-formaldehyde denaturing gel. Depending on the source and the isolation procedure, 1 to 15 µg RNA per lane is loaded. RNA is transferred to Hybond-XL nylon membrane and hybridized with [$^{32}$P] labeled (CAG)7 or control oligonucleotides. Prior to the Northern blot analysis, selected samples are treated with either RNaseR or RNaseH. For RNase R treatment, RNA is incubated at oligomers at 37° C. for 30 min in 20 mM M Tris-HCl (pH 8.0), 100 mM KCl, 0.1 mM $MgCl_2$ and 1 U/µl RNaseR (Epibio). For RNaseH, RNA is incubated with intron-specific oligomers at 37° C. for 30 min prior to treatment with 0.03 U/ml RNaseH (Invitrogen), 1 U/ml RNasin (Promega), 0.27 mg/ml BSA (Promega) and 10 mM DTT at 37° C. for 30 min. RNase-treated samples are phenol-extracted and ethanol-precipitated prior to Northern blot analysis.

Figure 4:
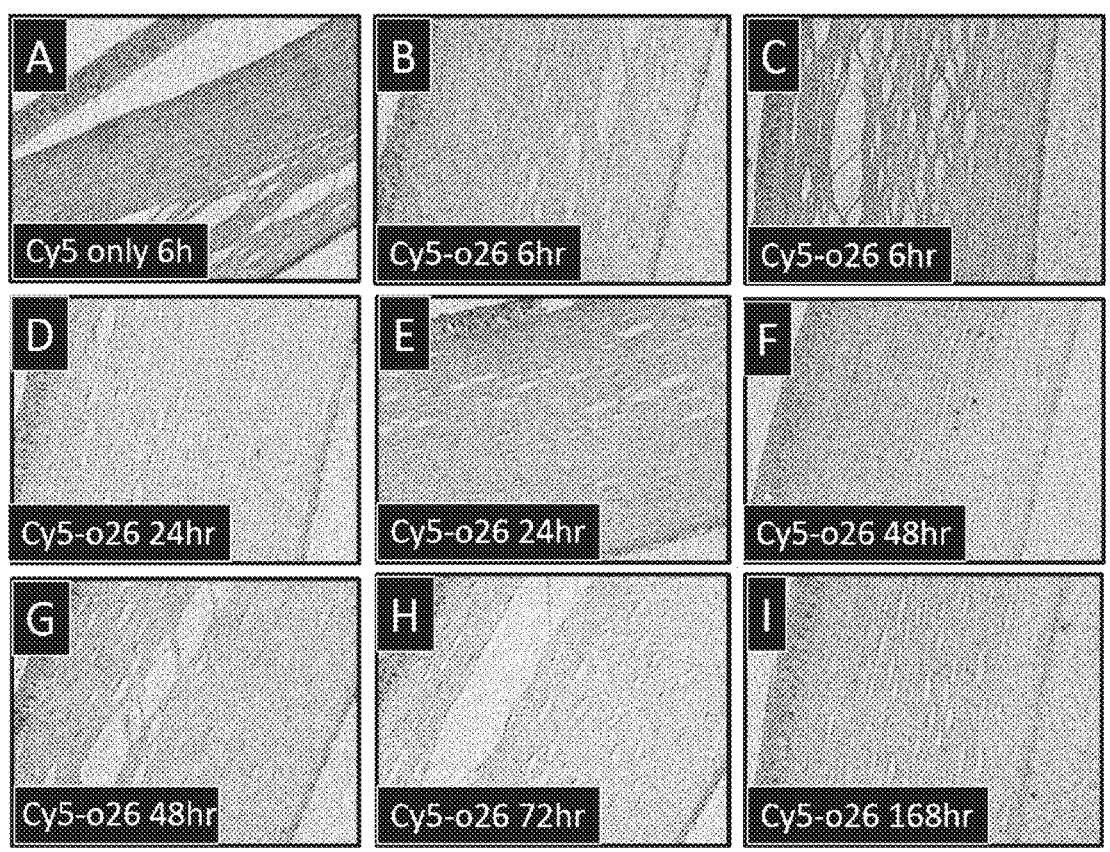
FIG. 4 shows a time dependent increase in fluorescence associated with the corneal endothelium and an overall increase in fluorescence of the corneal stroma after intravitreal injection of Cy5-labelled oligonucleotide into a rabbit's eye.

Example 2. Targeting the Corneal Endothelial Cell Layer Using Therapeutic Oligonucleotides To investigate whether oligonucleotides could enter the corneal endothelium, ten Female Dutch Belted Rabbits were given a single intravitreal administration into both eyes of Cy-5-labelled oligonucleotide (with sequence unrelated to the present invention) utilizing 2'-O-methyl modifications at a single dose of 0.6 mg in 30 µl of PBS at a concentration of 20 mg/ml. Two rabbits were sacrificed at each time-point (6, 24, 48, 72 and 168 hour following intravitreal injection) by an intravenous injection of sodium pentobarbitone and exsanguination. Eyes were subsequently removed and placed into modified Davidson's fluid for fixation. Histological slides were then prepared and stained with Hematoxylin and eosin and then examined on a fluorescent microscope to specifically note structures within the eye that were associated with increased fluorescence which would reflect accumulation of labelled oligonucleotide (FIG. 4). The Cy-5-labelled oligo gave staining at 6 hour versus Cy-5 alone that served as the control. No staining was visible with the Cy-5 control at the 6 hour time point. Hence, the conclusion was that the uptake was through the oligo, not via the Cy-5 label. Maximal uptake was observed already at the 48 hour time point.

The entry of therapeutic oligonucleotides into ocular cellular structures has been noted previously without the aid of transfection reagents which are generally used in in vitro situations. The inventors of the present invention have recently found that in vivo transfection excipients can augment the entry of potentially therapeutic oligonucleotides to a variety of tissues when co-administered systemically with potentially therapeutic oligonucleotides (data not shown).

Example 3. TCF-4 Targeted Therapeutic Oligonucleotide Reduces RNA Foci in FECD CEC Predicted therapeutic oligonucleotide comprising a repeated CAG sequence with seven repeats ((CAG)7) was also shown to reduce RNA foci in human corneal endothelial cells derived from an FECD patient with a heterozygous expansion of greater than 40 CUG repeats. The allelic CUG TNR repeats were found to be 12 and 52 in the patient's TCF4 gene. Corneal endothelial cells were derived from this patient using methods known in the art (Peh et al. 2013 BMC Res Notes 6:176; Peh et al. 2015 Sci Rep 5:9167), and the effect of reducing RNA foci in these cells was investigated upon transfecting (CAG)7 into the in vitro held cells. Therapeutic oligonucleotide was used at a concentration of 200 nM and transfected with Dharmafect (0.5 ul per well as per manufacturer's instructions) for 24 hrs. Then, cells were fixed and subjected to FISH with a Cy3-labelled (CAG)7 oligonucleotide probe (performed as noted in Example 1) and viewed on a confocal microscope.

FIG. 5 shows the effect of therapeutic oligonucleotide (CAG)7 in reducing RNA foci (pink spots) in the corneal endothelial cells. The upper three panels are treated cells, the lower three panels are cells treated with control oligonucleotide. Therapeutic oligonucleotide was used at a concentration of 200 nM and transfected with Dharmafect. The number of RNA foci in the nuclei was determined by automated image analysis and displayed in FIG. 5 as a histogram (bottom of the figure). Specifically, FISH-labelled RNA foci were quantified with a segmentation-based approach using CellProfiler™ ver 2.1.1 (Broad Institute). Briefly, nuclei were defined in the 405 nm channel using maximum correlation thresholding. RNA foci were defined in the 568 nm channel as objects within 2 and 10 pixels using the Robust Background algorithm per individual masking objects (nuclei) with a smoothing scale of 2.0, threshold correction factor of 1.45 and lower and upper bounds set to 0.05 and 1.0. Data was further processed using Microsoft Excel.

As can be observed from both the micrographs and the histogram the therapeutic oligonucleotide (CAG)7 was effective in reducing the number of RNA foci compared to transfection of a control (irrelevant) oligonucleotide (in the histogram referred to as 'untreated'). This shows that the method of the present invention is applicable in human corneal endothelial cells from an FECD patient.

Figure 6:
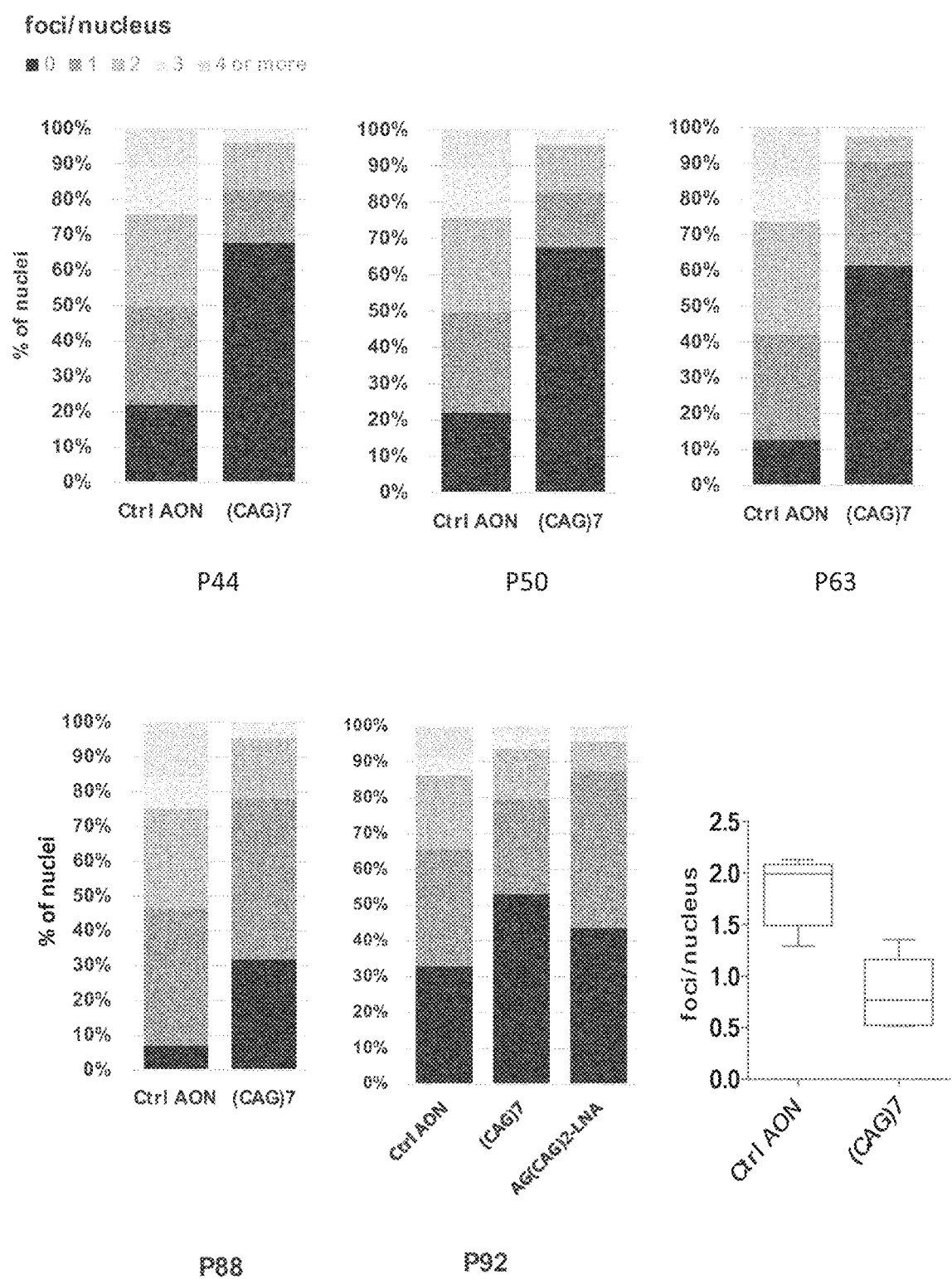
FIG. 6 shows the effect of therapeutic oligonucleotide (CAG)7 in reducing RNA foci in human corneal endothelial cells derived from five different FECD patients (P44, P50, P63, P88, and P92) with a heterozygous expansion of greater than 40 CUG repeats in the TCF4 gene. Experiment is the same as for FIG. 5, but now for cells from these five additional five patients. Each histogram represents a single patient. AG(CAG)2-LNA is an additional AON that was tested once, in cells from the fifth patient only. It appeared that this AON with this sequence and in a locked nucleic acid (LNA) configuration was inferior to the (CAG)7 AON. The graph on the right shows the average foci per nucleus when the results of all five patients are taken together. 'ctrl AON' means treatment with a control unrelated oligonucleotide.

This experiment was then repeated in five independent FECD patient samples with at least one TCF4 allele containing more than 40 TNR repeats. The results of these experiments are shown in FIG. 6; each histogram representing a different patient. Similar to what is seen in FIG. 5, the number of foci decreases upon treatment with the (CAG)7 therapeutic oligonucleotide in comparison to the control antisense oligonucleotide (ctrl AON): the percentage of nuclei that do not have foci or limited numbers of foci increases. In cells from the fifth patient an additional oligonucleotide was used, which was a AG(CAG)2 AON in a locked nucleic acid (LNA) configuration. This particular chemistry and sequence appeared inferior the (CAG)7 repeat. The graph on the right shows the average number of foci per nucleus with the data from these five patients taken together, showing the significant effect of the AON of the present invention on reducing foci in the retina.

The invention claimed is:

1. A method of treating or preventing Fuchs Endothelial Corneal Dystrophy (FECD) caused by a 5'-(CUG)$_n$-3' trinucleotide repeat (TNR) expansion in a pre-mRNA transcript of the TCF4 gene, in a human subject in need thereof, wherein n is an integer of 40 or greater, the method comprising administering to the subject a single-stranded antisense oligonucleotide or a delivery vehicle encoding the oligonucleotide, wherein the oligonucleotide is at least partially complementary to and capable of binding the TNR expansion,
   wherein the oligonucleotide or delivery vehicle is administered to the corneal stroma of the human subject by intrastromal injection, to the anterior chamber fluid of the human subject by intracameral injection, or to the posterior chamber of the human subject by intravitreal injection, and
   wherein the oligonucleotide comprises a sequence selected from the group consisting of SEQ ID NO: 3, 4, 5, 6, 7, 8, 9, 10, 11, 12, 13, 14, 15, CAGCAGCAG, AGCAGCAGC, and GCAGCAGCA.

2. The method of claim 1, wherein n is an integer of 50 or greater.

3. The method of claim 1, wherein all nucleotides of the oligonucleotide are 2'-O methyl phosphorothioate ribonucleotides or 2'-O methoxyethyl phosphorothioate ribonucleotides.

4. The method of claim 1, wherein the oligonucleotide comprises the sequence 5'-(CAG)$_m$-3', wherein m is an integer selected from 8, 9, 10, 11, 12, 13, 14, 15, 16 and 17.

5. The method of claim 1, wherein the oligonucleotide comprises SEQ ID NO: 3.

6. The method of claim 1, wherein the oligonucleotide consists of SEQ ID NO: 3.

\* \* \* \* \*

SEQUENCE LISTING

```
<160> NUMBER OF SEQ ID NOS: 16

<210> SEQ ID NO 1
<211> LENGTH: 1752
<212> TYPE: DNA
<213> ORGANISM: Homo sapiens
<220> FEATURE:
<221> NAME/KEY: exon
<222> LOCATION: (1)..(30)
<223> OTHER INFORMATION:
<220> FEATURE:
<221> NAME/KEY: intron
<222> LOCATION: (31)..(1722)
<223> OTHER INFORMATION:
<220> FEATURE:
<221> NAME/KEY: repeat_unit
<222> LOCATION: (848)..(921)
<223> OTHER INFORMATION: CTG trinucleotide repeat
<220> FEATURE:
<221> NAME/KEY: exon
<222> LOCATION: (1723)..(1752)
<223> OTHER INFORMATION:
```

<400> SEQUENCE: 1

```
gagctgagtg atttactgga tttcagtgcg gtaagaaaga acggtggaaa ctaacaacag      60
ctgtgaaaaa aacaaaacaa aaacccaaac acttcagcta gaaaccagta ggaatctaaa     120
ggacagtaat aattttaat tggctgaatc cttggtaaat atgaaggtct ttttgacaag      180
ttttaacta taattttgtg gtgtgatgga agattcaggc tttttttttt ttttgagttt      240
tattactggc cttcaattcc ctacccactg attaccccaa ataatggaat ctcaccccag     300
tggaaagcaa aaatagacac ccctaaaact aaaccacccc taaaacttgg ccatgtctga     360
acactgagac tactaatact ttgcacacta ctcttcgttt tatttattgt ttttggaaat     420
ggaaaataga aaataggaga cccagttgtc tctttaaagt tttaagctaa tgatgctttg     480
gattggtagg acctgttcct tacatcttac ctcctagtta catcttttcc taggattctt     540
aaaactagta tggatatgct gagcatacat tctttagaac cttttggact gttttggtaa     600
atttcgtagt cgtaggatca gcacaaagcg gaacttgaca cacttgtgga gttttacggc     660
tgtacttggt ccttctccat ccctttgctt ccttttccta aaccaagtcc cagacatgtc     720
aggagaatga attcattttt aatgccagat gagtttggtg taagatgcat ttgtaaagca     780
aaataaaaag aatccacaaa acacacaaat aaaatccaaa ccgccttcca agtgggctc     840
tttcatgctg ctgctgctgc tgctgctgct gctgctgctg ctgctgctgc tgctgctgct     900
gctgctgctg ctgctgctgc tcctcctcct cctcctcctt ctcctcctcc tcctcctctt     960
ctagaccttc ttttggagaa atggctttcg gaagttttgc caggaaacgt agccctaggc    1020
aggcagcttt gcagccccct ttctgcttgt tgcactttct ccattcgttc ctttgctttt    1080
tgcaggctct gactcaggga aggtgtgcat tatccactag atacgtcgaa gaagagggaa    1140
accaattagg gtcgaaataa atgctggaga gagagggagt gaaagagaga gtgagagtga    1200
gagagagaga gagtcttgct tcaaattgct ctcctgttag agacgaaatg agaatttagt    1260
gcaggtggca cttttatttt tatttgggtt cacatatgac aggcaaatcc tatacgagat    1320
ggaaatggac attgccacgt ttatggccaa ggttttcaat ataaaacaaa acaactttt     1380
tcttctcctt ggtgaaacta gtgtttttct agagaggctg ctggcctcca acctgaatct    1440
tgataacatt atggggactg tgtttgttcc aaatgtagca gtagtactgc ttggccatct    1500
aatgaacctg aggaaaaaga aagaacagag tgataatggg ggctggggtg ggatctgtaa    1560
tgttgtttct cttttagttt taagttggat ggtgatgtat tttactaaat aaacccttag    1620
cataaactct aagctgtttg gtaacagtat gaaagatctt tgaggagctc tgaaggcaca    1680
agtgtcttct tttcaactgt aatatttctt tgtttctttt agatgttttc acctcctgtg    1740
agcagtggga aa                                                       1752
```

<210> SEQ ID NO 2
<211> LENGTH: 21
<212> TYPE: RNA
<213> ORGANISM: Homo sapiens

<400> SEQUENCE: 2

```
cugcugcugc ugcugcugcu g                                                21
```

<210> SEQ ID NO 3
<211> LENGTH: 21
<212> TYPE: RNA
<213> ORGANISM: Artificial Sequence
<220> FEATURE:
<223> OTHER INFORMATION: antisense oligonucleotide

```
<400> SEQUENCE: 3
cagcagcagc agcagcagca g                                              21

<210> SEQ ID NO 4
<211> LENGTH: 18
<212> TYPE: RNA
<213> ORGANISM: Artificial Sequence
<220> FEATURE:
<223> OTHER INFORMATION: antisense oligonucleotide

<400> SEQUENCE: 4
cagcagcagc agcagcag                                                  18

<210> SEQ ID NO 5
<211> LENGTH: 15
<212> TYPE: RNA
<213> ORGANISM: Artificial Sequence
<220> FEATURE:
<223> OTHER INFORMATION: antisense oligonucleotide

<400> SEQUENCE: 5
cagcagcagc agcag                                                     15

<210> SEQ ID NO 6
<211> LENGTH: 12
<212> TYPE: RNA
<213> ORGANISM: Artificial Sequence
<220> FEATURE:
<223> OTHER INFORMATION: antisense oligonucleotide

<400> SEQUENCE: 6
cagcagcagc ag                                                        12

<210> SEQ ID NO 7
<211> LENGTH: 21
<212> TYPE: RNA
<213> ORGANISM: Artificial Sequence
<220> FEATURE:
<223> OTHER INFORMATION: antisense oligonucleotide

<400> SEQUENCE: 7
agcagcagca gcagcagcag c                                              21

<210> SEQ ID NO 8
<211> LENGTH: 18
<212> TYPE: RNA
<213> ORGANISM: Artificial Sequence
<220> FEATURE:
<223> OTHER INFORMATION: antisense oligonucleotide

<400> SEQUENCE: 8
agcagcagca gcagcagc                                                  18

<210> SEQ ID NO 9
<211> LENGTH: 15
<212> TYPE: RNA
<213> ORGANISM: Artificial Sequence
<220> FEATURE:
<223> OTHER INFORMATION: antisense oligonucleotide

<400> SEQUENCE: 9
agcagcagca gcagc                                                     15

<210> SEQ ID NO 10
```

-continued

```
<211> LENGTH: 12
<212> TYPE: RNA
<213> ORGANISM: Artificial Sequence
<220> FEATURE:
<223> OTHER INFORMATION: antisense oligonucleotide

<400> SEQUENCE: 10
agcagcagca gc                                                         12

<210> SEQ ID NO 11
<211> LENGTH: 21
<212> TYPE: RNA
<213> ORGANISM: Artificial Sequence
<220> FEATURE:
<223> OTHER INFORMATION: antisense oligonucleotide

<400> SEQUENCE: 11
gcagcagcag cagcagcagc a                                               21

<210> SEQ ID NO 12
<211> LENGTH: 18
<212> TYPE: RNA
<213> ORGANISM: Artificial Sequence
<220> FEATURE:
<223> OTHER INFORMATION: antisense oligonucleotide

<400> SEQUENCE: 12
gcagcagcag cagcagca                                                   18

<210> SEQ ID NO 13
<211> LENGTH: 15
<212> TYPE: RNA
<213> ORGANISM: Artificial Sequence
<220> FEATURE:
<223> OTHER INFORMATION: antisense oligonucleotide

<400> SEQUENCE: 13
gcagcagcag cagca                                                      15

<210> SEQ ID NO 14
<211> LENGTH: 12
<212> TYPE: RNA
<213> ORGANISM: Artificial Sequence
<220> FEATURE:
<223> OTHER INFORMATION: antisense oligonucleotide

<400> SEQUENCE: 14
gcagcagcag ca                                                         12

<210> SEQ ID NO 15
<211> LENGTH: 21
<212> TYPE: RNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(3)
<223> OTHER INFORMATION: n is a, c, g, or u
<220> FEATURE:
<221> NAME/KEY: modified_base
<222> LOCATION: (6)..(6)
<223> OTHER INFORMATION: I
<220> FEATURE:
<221> NAME/KEY: misc_feature
```

```
<222> LOCATION: (6)..(6)
<223> OTHER INFORMATION: n is a, c, g, or u
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: n is a, c, g, or u
<220> FEATURE:
<221> NAME/KEY: modified_base
<222> LOCATION: (12)..(12)
<223> OTHER INFORMATION: I
<220> FEATURE:
<221> NAME/KEY: misc_feature
<222> LOCATION: (12)..(12)
<223> OTHER INFORMATION: n is a, c, g, or u
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(15)
<223> OTHER INFORMATION: n is a, c, g, or u
<220> FEATURE:
<221> NAME/KEY: modified_base
<222> LOCATION: (18)..(18)
<223> OTHER INFORMATION: I
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: modified_base
<222> LOCATION: (21)..(21)
<223> OTHER INFORMATION: I
<220> FEATURE:
<221> NAME/KEY: misc_feature
<222> LOCATION: (21)..(21)
<223> OTHER INFORMATION: n is a, c, g, or u

<400> SEQUENCE: 15
cancancanc ancancanca n                                              21

<210> SEQ ID NO 16
<211> LENGTH: 21
<212> TYPE: RNA
<213> ORGANISM: Artificial Sequence
<220> FEATURE:
<223> OTHER INFORMATION: antisense oligonucleotide

<400> SEQUENCE: 16
cugcugcugc ugcugcugcu g                                              21
```